United States Patent [19]

Sealfon

[11] Patent Number: 4,921,480

[45] Date of Patent: May 1, 1990

[54] FIXED VOLUME INFUSION DEVICE

[76] Inventor: Andrew I. Sealfon, Rte. #3, Box 61, Middletown, N.Y. 10940

[21] Appl. No.: 274,327

[22] Filed: Nov. 21, 1988

[51] Int. Cl.[5] ............................................ A61M 31/00
[52] U.S. Cl. ......................................... 604/65; 604/67
[58] Field of Search ..................... 604/65, 66, 67, 121, 604/122, 123, 151, 152, 153

[56] References Cited

U.S. PATENT DOCUMENTS

| 4,467,844 | 8/1984 | Di Gianfilippo et al. | 604/65 X |
| 4,820,268 | 4/1989 | Kawamura et al. | 604/65 X |
| 4,838,856 | 6/1989 | Mulreany et al. | 604/67 X |
| 4,838,857 | 6/1989 | Strowe et al. | 604/67 |

*Primary Examiner*—John D. Yasko

[57] ABSTRACT

In a gravity feed intravenous fluid delivery system, a fixed volume metering valve having an upwardly spring biased fluid-measuring piston that is also downwardly pressure biased and is effective to cause the dispensing of a fixed volume of intravenous fluid for each up and down cycle of piston movement, characterized by a cyclically operated clamp on the delivery tube of the system which, when the clamp is closed, allows the spring bias to lift the piston in ascending movement and, when in an open clamp condition, causes the pressure to urge the piston in descending movement, to thereby produce said up and down piston movement which cyclically dispenses the fixed volume of intravenous fluid.

16 Claims, 1 Drawing Sheet

FIXED VOLUME INFUSION DEVICE

The present invention relates to gravity feed intravenous fluid delivery systems as used in hospitals, and more particularly to such systems enhanced with metering valves to provide more precise control over the volume of intravenous fluid delivered to the patient.

THE PRIOR ART

An intravenous fluid patient-feeding system relying only on gravity flow from an elevated source to the patient must of necessity exhibit different flow rates as the amount, and thus the "head", of the intravenous fluid diminishes over its period of use. These systems are accordingly typically enhanced by fixed volume chamber in-line metering valves which are alternately filled and emptied to deliver the selected "fixed volume" in incremental fashion to the patent. Although generally useful for the purpose intended, these prior art fixed volume metering valves have shortcomings that are belied by the apparent simplicity of their operating mode. For example, incident to emptying the fixed volume chamber preparatory to the delivery therefrom to the patient of the "fixed volume" of intraveneous fluid, the feed tube must be clamped closed upstream, i.e. between the source and the valve, and subsequently incident to refilling the fixed volume chamber, the tube must be clamped closed downstream, i.e. between the valve and the patient. Even more significant, during refilling of the fixed volume chamber, the chamber must be vented of air without undermining the sterile condition of the system and with a safeguard that the air being vented is not permitted into the patient's vascular system.

EXAMPLE OF THE PRIOR ART

In U.S. Pat. No. 4,262,668 issued on Apr. 21, 1981 to Schmidt, there is shown a gravitational intravenous fluid system in which a fixed volume chamber of an in-line metering valve, alternately filled and emptied, provides incremental amounts of the intravenous fluid to the patent. When the fixed volume chamber is filled, strategically located hydrophobic and hydrophilic filters 30,32, respectively allow the safe venting to atmosphere of air from the chamber, while preventing any of the air from entering the patient's vascular system.

In contrast to the foregoing, the inventive metering valve similarly provides the advantages of incremental feed of a fixed volume chamber, but totally obviates the need of venting the chamber incident to the refilling thereof during each cycle of use. The operational mode contemplates, unlike Schmidt and all other known prior art, that piston movement will clear the fixed volume chamber, and will be urged in the movement necessary to do so, as well as in the reverse direction necessary to cyclically repeat this movement, without the need for any of the referenced prior art filters or attendant complications in alternately filling and emptying the fixed volume chamber.

In accordance with the present invention, the operating mode of the within metering valve contemplates that the piston thereof will be urged in descending movement from a starting "upper" position (the orientation of the system also being vertical for gravity feed) to a "down" or ending home position, and that such descending piston movement will deliver a precise selected amount of intravenous fluid, and that the aforesaid will be against the opposing bias or urgency of a return spring which thereafter will cause reverse ascending direction movement of the piston from said "down" back to said "upper" position. Underlying the present invention is the recognition that although the return spring urgency is of necessity selected to be less than the "static" head of the elevated intravenous source, that it can nevertheless cause ascending piston movement if the intravenous flow is interrupted and the pressure gradient for flow from the source to the patient is removed. In such a circumstance, which, according to the present invention, is provided by clamping closed the intravenous tubing, but only during the required return spring functioning part of the operating cycle, the return spring bias although less than the "head" causes ascending movement of the piston operating in the then, non-moving or flowing intravenous fluid. The cycle of the operating mode of the metering valve is then repeated by opening the referred to clamp and restoring the pressure gradient of the higher pressure head of the intravenous fluid source in communication with the lower pressure of the patient, thereby resulting in flow from said source to the patient.

The description of the invention which follows, together with the accompanying drawings should not be construed as limiting the invention to the example shown and described, because those skilled in the art to which this invention appertains will be able to devise other forms thereof within the ambit of the appended claims.

Figure 1:
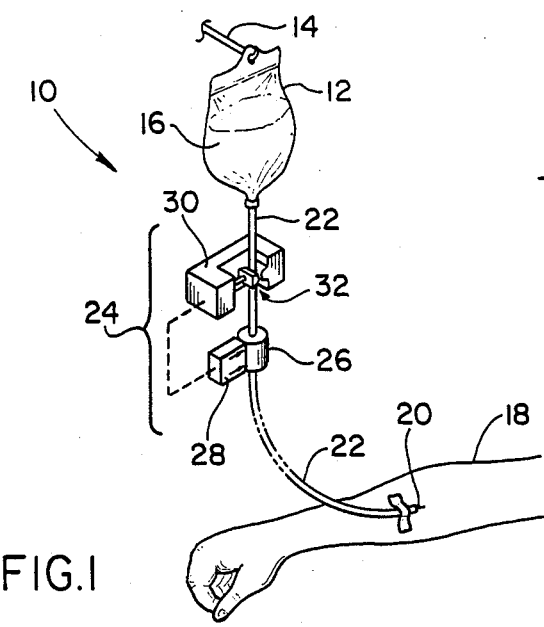
FIG. 1 is a perspective view of a typical intravenous fluid delivery system including as a component thereof the within inventive intravenous fluid metering valve.

Shown in FIG. 1 is a typical hospital intravenous fluid delivery system 10 for saline solution or the like, including a usual plastic bag intravenous fluid container 12 suspended from a support 14, and having valve control means 24 to regulate the flow of fluid 16 which is delivered to the patient 18 via a conventional luer connector and catheter or needle 20 and tubing 22.

Of particular interest to this invention is the manner in which the flow control valve means 24 is designed to deliver a precise volume of fluid 16 over a specific period of time to the patient 18.

Control means 24 is comprised of a metering valve 26, a sensor means 28, and an electronic control system 30 and solenoid clamp 32.

Figure 2:
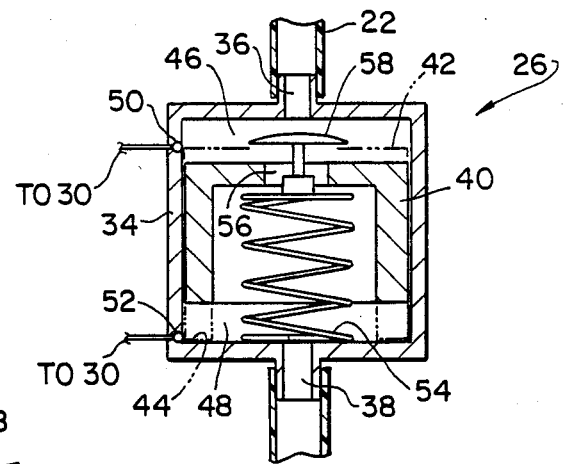
FIG. 2 is an isolated cross sectional view, on an enlarged scale, of the metering valve.

Valve 26, located actually in the flow path of the tubing 22 is shown in isolated cross section in FIG. 2 to include a housing 34 having at opposite ends an inlet 36 and an outlet 38. When solenoid clamp 32 is open, and a pressure gradient exists to allow flow through the tubing 22, the higher pressure of this pressure gradient in the specific form of static pressure from fluid 16 forces piston 40 from an initial "upper" ready position 42 to a "down" home position 44. As a result of this piston movement, fluid 16 enters the upper part 46 of housing 34 and displaces fluid 16 from the lower part of housing 34 such that said displaced fluid flows to the vascular system of the patient 18. Housing 34 supports upper sensor 50 and lower sensor 52 which detect the position of piston 40. When piston 40 is in position 42, control circuit 30 soon to be described in detail, interprets this valve position as indicating "valve ready for cycling", and when piston 40 reaches position 44, its "down" position, circuit 30 gives the signal to close solenoid clamp 32.

Piston 40 is continuously biased upwardly by a helical spring 54 and when solenoid clamp 32 is closed, piston 40 ascends under this spring bias so that fluid 16 gradually transfers through a passageway 56 under seal 58 from an upper compartment 46 to a lower compartment 48. Seal member 58 closes opening 56 during descending movement of piston 40 so that fluid in the compartment 48 is effectively urged through the outlet 38.

Figure 3:
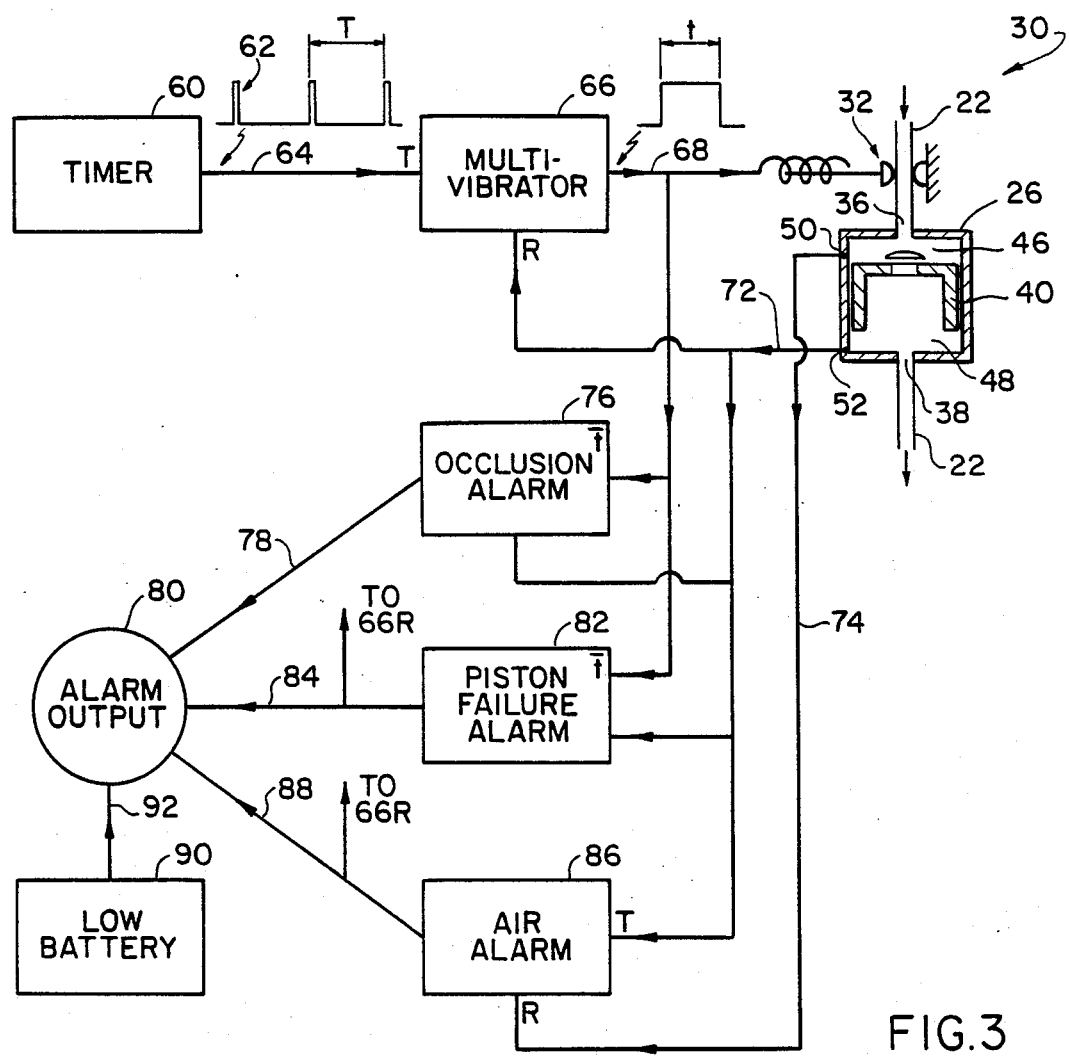
FIG. 3 is a block diagram of an electronic circuit which monitors the operating mode of the metering valve.

The operating mode of valve 26 as above described, and more particularly the sensing of the "upper" and "down" positions and movement therebetween of the piston 40 is advantageously used to monitor the operating mode of the valve 26 in conjunction with a control circuit 30 as shown in FIG. 3, so that any malfunctioning thereof is communicated as an alarm condition, such as, for example, conditions indicative (1) of an occlusion or blockage in the valve 26, (2) of non-cyclical movement of the valve piston 40 and (3) of air entering the flow passage of the system, as well as other undesirable operating conditions.

Operation of the valve 26 is controlled by an electronics system 30, which may be battery powered, which both controls the flow rate of the valve 26 and provides a system of monitors to insure proper valve operation. As depicted in FIG. 3, valve flow rate is controlled by timer 60, which may be an astable multivibrator or other known type of circuitry adapted to provide a series of relatively short duration trigger pulses 62 on a continuous basis on line 64. As the valve 26 is designed to provide a discrete volume of fluid per operating cycle, valve output per unit time may be controlled by the choice of the pulse rate for timer 60. For example, if 60 milliliters per hour is to be dispensed through a 0.2 milliliter volume valve chamber, a pulse repetition rate of 1 pulse every 5 seconds is required (60 ml/hr/.2 ml/pulse = 300 pulse/hr = 1 pulse/5 sec ). With appropriate drive circuitry, the output pulses may be varied over a given time frame to provide a variable dosage rate as may be required.

The output pulses 62 are applied to the trigger terminal of multivibrator or oneshot circuitry 66, whose output on line 68 goes high for a predetermined time t and then returns to the low state to await the next trigger pulse from timer 60. The time t is chosen to correspond to the maximum time allowable for the valve piston 40 to move from its upper, ready position 42 to its lower home position 44, and is chosen with consideration of valve characteristics and metered fluid viscosity. The pulse on line 68 is used to activate solenoid clamp 32, which opens tubing 22 to the inlet 36 of valve 26 allowing fluid 16 to enter the valve chamber 46 and drive the fluid in chamber portion 48 to outlet 38 and patient 18.

When the upper valve chamber 46 is completely filled, resulting in the piston being driven to the home position 44 and in the dispensation of the measured volume of fluid in valve chamber 48, a home signal pulse is generated on line 72. This pulse may be created by a piston sensor 52 utilizing optical, magnetic, mechanical or other sensing methods as known in the art. Similar pulse circuitry in pulse sensor 50 is utilized to indicate piston positioning at the upper ready position 42, and is outputted on line 74. Line 72 is coupled to the reset terminal R of multivibrator 66, to terminate the multivibrator output on line 68, deenergizing solenoid clamp 32 and terminating the fill of the valve chamber 46. As used herein, the term "reset" refers to the termination of the output of multivibrator 66 with a return to the stable state, rather than a reset and immediate restart of the multivibrator output. Upon reset and flow termination the piston 40 is driven by the valve spring 54 to the ready position 42, the measured volume of fluid 16 is transferred into valve chamber 48 from chamber 46, and the system awaits the next load signal 62 from timer 60.

If no home signal on line 72 is produced in the maximum operating time established by the length of time of the pulse on line 68, an alarm condition exists, indicative of an occlusion or blockage in the valve 26 preventing piston 40 operation. This condition is sensed by occlusion alarm circuitry 76, which may be formed around a multivibrator timer. The leading edge of the pulse on line 68 serves as the trigger, while the home pulse on line 72 resets the timer circuit. If a reset pulse is not received by the end of the timing cycle an output on line 78 activates alarm output unit 80, which may be a piezoelectric device, light or the like. The timing cycle for occlusion alarm 76 is chosen to correspond to the pulse length.

If the piston 40 operates without a pulse on line 68, or if it remains at the home position 42 for an extended period of time, a second failure mode exists. This is sensed by failure alarm circuitry 82, which may be formed around comparators providing an alarm-activating output on line 84 whenever line 72 is high, indicating the piston being at the home position 42, without a high signal on line 68, indicating a solenoid-energized condition. In addition, circuitry 82 may include timer circiutry to compare the length of the line 68 output to a reference. If the reference time is exceeded, the output on line 84 is activated. In addition, a reset signal may be sent to timer 66, insuring the solenoid clamp 32 is disabled to prevent fluid 16 beyond that in the valve chamber 48 from reaching the patient 18.

In the event air enters the system and enters the valve chamber 46, a third alarm condition exists. This condition is sensed by alarm circuitry 86, which may include circuitry which compares the time for piston 40 to return from its home position 44 to its ready position 42 to a preset standard. When air enters the chamber 46 the piston return time decreases, as system viscosity lessens. The alarm circuitry 86 may be designed around a multivibrator, triggered by the home signal on line 72. If no reset pulse on line 74, indicating return of the piston 40 to the ready position 42, is received by the end of the timing cycle to disable the multivibrator 86, an output on line 88 activates alarm 80. This output may also be applied to the reset of timer 66, halting solenoid clamp 32 operation to prevent the valve air from being forced out of the valve 26 to the patent 18 by the pressure of the fluid 16 entering the valve chamber 46.

Alarm output device 80, shown as coupled to each alarm sensor, may be replaced with three separate alarm devices to distinguish between the different alarm conditions. Other or additional known circiutry may also be used to provide specific data to the operator as to the alarm condition experienced. In addition, low battery sense circuiutry 90 may be coupled to output device 80 by line 92. Further, timing means 10 may be disconnected from the remainder of the circuitry in an alarm condition to prevent operation until the alarm condition is corrected and the system manually reset.

Although as described herein the inventive fixed volume metering valve is particularly advantageously used in a gravitational intravenous fluid system as illustrated in FIG. 1, it also is useful for a system in which a spring-operated pump, such as is illustrated and described in U.S. Pat. No. 4,447,232 issued to Sealfon et al. on May 8, 1984, is substituted for the static pressure head provided by the elevated support 14.

While the particular metering valve-functioning as a fixed volume infusion device and the operational method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. For use with a gravitational intravenous fluid system of the type in which intravenous fluid from an elevated source flows by gravity through tubing defining a flow passage under a pressure gradient to a vascular system of a patient, said pressure gradient being a higher static pressure of said intravenous fluid source in relation to a lower pressure of said patient vascular system, a fixed volume metering valve for providing incremental flow of said intravenous fluid comprising a housing bounding a chamber for a piston having an inlet at an upper end thereof in communication with said intravenous fluid source and at a lower opposite end an outlet in communication with said patient vascular system, an inverted U-shaped piston having three legs cooperating to bound therebetween a compartment and operatively disposed for opposite direction sliding movement in said chamber between an upper position of movement established by a horizontally oriented leg of said piston being adJacent said inlet and a lower position of movement established by the vertically oriented other two legs thereof being adJacent said outlet, a piston return spring disposed in said piston compartment so as to bias said piston in ascending movement from said lower to said upper position of movement, said ascending piston movement being normally prevented by said pressure gradient urging said piston in descending movement from said upper to said lower position of movement, and a normally open clamp operatively arranged to cyclically clamp closed said tubing so as to remove said pressure gradient from said flow system, whereby in response to said open condition of said clamp, said pressure gradient urges said piston in descending movement causing the dispensing of a selected fixed volume of intravenous fluid by said piston and in response to said closed clamp condition, said spring urges said piston in ascending movement, incident to repeating the fluid dispensing functioning thereof to thereby enable said metering valve to provide successive incremental intravenous fluid flow in selected fixed amounts through said gravitational intravenous fluid system.

2. The fixed volume metering valve for a gravitational intravenous fluid system as claimed in claim 1 wherein a clearance is selected to be of a size within said piston chamber above said horizontally oriented leg of said piston in said lower position of movement thereof to form a fixed volume chamber for correspondingly providing a fixed amount of intravenous fluid to be dispensed by said metering valve, said intravenous fluid in said fixed volume chamber being displaced to said piston compartment during piston ascending movement and thereafter urged through exiting movement therefrom to said patient during piston descending movement.

3. The fixed volume metering valve for a gravitational intravenous fluid system as claimed in claim 2 including piston position of movement sensing means in said piston housing adjacent said piston upper and lower positions of movement, and alarm means operatively arranged to be operated by said sensing means responsive to the piston position of movement as sensed by said sensing means, to thereby contribute to controlling the successive incremental intravenous fluid dispensing service of said metering valve.

4. A control system for operating a fluid dispensing unit having a piston movable within a housing from a ready position to a home position to pass a measured volume of fluid through the unit, comprising: a timer adapted to generate a series of timing signals, said signals defining the dispensing rate of the unit; pulse generating means operatively connected to said timer for generating a drive signal of predetermined length in response to receipt of a timing signal; valve means operatively connected to said pulse generating means for passing fluid to said piston housing during the duration of said drive signal; ready and home position sensors mounted to said housing for sensing the ready and home positions, respectively, of said piston and generating an output responsive thereto; and alarm means operatively connected to said pulse generating means and ready and home sensors to generate an alarm signal when a combination of drive signal, ready sensor output and home sensor output indicates an improper operating condition.

5. The apparatus of claim 4 wherein said alarm means comprises an occlusion alarm operatively connected to said pulse generating means and home sensor for generating means and home sensor for generating and occlusion alarm signal if the end of said drive signal occurs prior to receipt of said home signal.

6. The apparatus of claim 4 wherein said alarm means comprises a piston failure alarm operatively connected to said pulse generating means and said home sensor for generating a piston failure signal when said home signal is present without said drive signal.

7. The apparatus of claim 4 wherein said alarm means comprises an air alarm operatively connected to said ready and home sensors for generating an air alarm signal when the time between receipt of said home signal and said ready signal exceeds a predetermined value.

8. The apparatus of claim 6 wherein said failure alarm further includes means to compare the length of said drive signal to a chosen reference value and to generate an alarm signal to a chosen reference value and to generate an alarm signal if said drive signal exceeds such value.

9. The apparatus of claim 6 wherein said piston alarm is operatively connected to said signal generating means whereby an alarm output places said signal generator means into a reset mode.

10. The apparatus of claim 7 wherein aid air alarm is operatively connected to said signal generating means whereby an alarm output places said signal generator into a reset mode.

11. The apparatus of claim 5 wherein said occlusion alarm comprises a multivibrator timer triggered by said drive signal and reset by said ready signal.

12. The apparatus of claim 6 wherein said failure alarm comprises comparators operatively connected to said ready and home position sensors.

13. The apparatus of claim 7 wherein said air alarm comprises a multivibrator triggered by said ready position sensor output and reset by said home position sensor output.

14. The apparatus of claim 4 wherein aid valve means comprises a solenoid valve.

15. A control system for operating a fluid dispensing unit having a piston movable within a housing from a ready position to a home position to pass a measured volume of fluid through the unit, comprising: a timer adapted to generate a series of timing signals, said signals defining the dispensing rate of the unit; pulse generating means operatively connected to said timer for generating a drive signal of predetermined length in response to receipt of a timing signal; valve means operatively connected to said pulse generating means for passing fluid to said piston housing during the duration of said drive signal; ready and home position sensors mounted to said housing for sensing the ready and home positions, respectively, of said piston and generating an output responsive thereto; an occlusion alarm operatively connected to said pulse generating means and home sensor for generating an occlusion alarm signal if the end of said drive signal occurs prior to receipt of said home signal; a piston failure alarm operatively connected to said signal generating means and said home sensor for generating an air alarm signal when the time between receipt of said home signal and said ready signal exceeds a predetermined value.

16. A fixed volume metering valve for providing incremental flow of intravenous fluid to a patient through a tubing connected between a source of said intravenous fluid and said patient comprising a housing bounding a chamber for a piston having an inlet at one end thereof in communication with said intravenous fluid source and at an opposite end an outlet in communication with said patient vascular system, an inverted U-shaped piston having three legs cooperating to bound therebetween a compartment and operatively disposed for opposite direction sliding movement in said chamber between a first position of movement established by a horizontally oriented leg of said piston being adjacent said inlet and a second position of movement established by the vertically oriented other two legs thereof being adjacent said outlet, a piston return spring disposed in said piston compartment so as to bias said piston in directional movement from said second to said first position of movement, said directional piston movement being normally prevented by a pressure gradient urging said piston in opposite directional movement from said first to said second position of movement, and a normally open clamp operatively arranged to cyclically clamp closed said tubing so as to remove said pressure gradient, whereby in response to said open condition of said clamp said pressure gradient urges said piston in said directional movement causing the dispensing of a selected fixed volume of intravenous fluid by said piston and in response to said closed clamp condition said spring urges said piston in said opposite directional movement incident to repeating the fluid dispensing functioning thereof to thereby enable said metering valve to provide successive incremental intravenous fluid flow in selected fixed amounts to said patient.

* * * * *